US012629465B2

(12) United States Patent
Baechler et al.

(10) Patent No.: US 12,629,465 B2
(45) Date of Patent: May 19, 2026

(54) SUCTION PUMP WITH OPTICAL STATUS INDICATOR

(71) Applicant: MEDELA AG, Baar (CH)

(72) Inventors: Cornel Baechler, Honau (CH); Thomas Imhof, Brittnau (CH); Hilmar Ehlert, Hergiswil (CH)

(73) Assignee: MEDELA AG, Baar (CH)

( * ) Notice: Subject to any disclaimer, the term of this patent is extended or adjusted under 35 U.S.C. 154(b) by 1005 days.

(21) Appl. No.: 17/420,969

(22) PCT Filed: Jan. 3, 2020

(86) PCT No.: PCT/EP2020/050090
§ 371 (c)(1),
(2) Date: Jul. 6, 2021

(87) PCT Pub. No.: WO2020/144116
PCT Pub. Date: Jul. 16, 2020

(65) Prior Publication Data
US 2022/0096726 A1 Mar. 31, 2022

(30) Foreign Application Priority Data

Jan. 9, 2019 (EP) ..................................... 19151005

(51) Int. Cl.
*A61M 1/06* (2006.01)
*A61M 1/00* (2006.01)

(52) U.S. Cl.
CPC .............. *A61M 1/73* (2021.05); *A61M 1/062* (2014.02); *A61M 2205/3389* (2013.01); *A61M 2205/584* (2013.01); *A61M 2205/587* (2013.01)

(58) Field of Classification Search
CPC ............ A61M 1/06–0697; A61M 1/14; A61H 9/0078
See application file for complete search history.

(56) References Cited

U.S. PATENT DOCUMENTS 6,728,464 B1 4/2004 Waldmann
8,287,507 B2 10/2012 Heaton et al.
(Continued)

FOREIGN PATENT DOCUMENTS

CN 107050548 A 8/2017
CN 206594967 U 10/2017
(Continued)

OTHER PUBLICATIONS

English translation of Tokoi (WO 2014162328) (Year: 2014).*
(Continued)

*Primary Examiner* — Courtney B Fredrickson
(74) *Attorney, Agent, or Firm* — MARSHALL, GERSTEIN & BORUN LLP

(57) ABSTRACT

The invention relates in one variant to a suction pump (1) for sucking body fluid, comprising an optical status indicator (5) for displaying a light signal as a function of the operating state of the suction pump (1), the optical status indicator (5) is arranged on at least two points of the outer surface of the suction pump (1), the surface normals of which are at an angle of at least 5° to one another. In a second variant, the invention relates to a suction pump (1) for sucking body fluid, including an optical status indicator (5) for displaying a light signal as a function of the operating state of the suction pump (1), wherein the suction pump (1) has on its underside at least one stand (13) for support on a support surface, the status indicator (5) is arranged on the underside of the suction pump (1) so that the light signal is emitted in the direction of the support surface. In a third variant, the invention relates to a suction pump (1) for sucking body fluid, including an optical status indicator (5) for displaying a light signal as a function of the operating state of the suction pump (1), the status indicator (5) occupying at least 5% of the surface of the suction pump (1).

12 Claims, 5 Drawing Sheets

(56) References Cited

U.S. PATENT DOCUMENTS

| | | | |
|---|---|---|---|
| 11,387,514 B2 | 7/2022 | Hiratsuka | |
| 2002/0085951 A1* | 7/2002 | Gelfand | A61M 1/36 |
| | | | 422/44 |
| 2010/0101212 A1 | 4/2010 | Iwachido et al. | |
| 2014/0276291 A1* | 9/2014 | Mansur, Jr. | A61H 9/0078 |
| | | | 601/152 |
| 2015/0369230 A1* | 12/2015 | Okumura | F04B 35/04 |
| | | | 417/63 |
| 2016/0055303 A1* | 2/2016 | Keller | G16H 40/63 |
| | | | 210/85 |
| 2017/0102846 A1* | 4/2017 | Ebler | G06F 3/04886 |
| 2017/0165405 A1 | 6/2017 | Muser et al. | |
| 2017/0234524 A1* | 8/2017 | Schäfer | A61M 1/1621 |
| | | | 362/572 |
| 2017/0319758 A1 | 11/2017 | Eddy et al. | |
| 2017/0330430 A1* | 11/2017 | Goodfield | A61G 7/05 |
| 2018/0005503 A1 | 1/2018 | Kaindl | |
| 2018/0104390 A1 | 4/2018 | Kilcran | |
| 2018/0318475 A1 | 11/2018 | Thomson et al. | |

FOREIGN PATENT DOCUMENTS

| | | | | | |
|---|---|---|---|---|---|
| DE | 10 2009 051 234 A1 | 5/2010 | | | |
| EP | 2371411 A1 | 10/2011 | | | |
| EP | 3 205 361 A1 | 8/2017 | | | |
| EP | 3228931 A1 | 10/2017 | | | |
| EP | 3326863 A1 | 5/2018 | | | |
| JP | 2007-245637 A | 9/2007 | | | |
| JP | 2017-170117 A | 9/2017 | | | |
| WO | WO-2014033686 A2 | 3/2014 | | | |
| WO | WO-2014162328 A1 * | 10/2014 | | A61M 1/367 |
| WO | WO-2015116743 A1 | 8/2015 | | | |
| WO | WO-2015197462 A1 | 12/2015 | | | |
| WO | WO-2017157691 A1 | 9/2017 | | | |
| WO | WO-2017196888 A1 | 11/2017 | | | |
| WO | WO-2018074446 A1 | 4/2018 | | | |

OTHER PUBLICATIONS

Japanese Translation Office Action for Application No. 2021-539591, dated Oct. 17, 2023.

Chinese Office Action for Application No. 202080008279.1, dated Oct. 26, 2023.

Office Action with Translation for a Japanese Patent Application No. 2021-539591, dated Oct. 4, 2022.

International Search Report for International Application No. PCT/EP2020/050090, mailed Apr. 6, 2020.

European Search Report for U.S. Appl. No. 19/151,005, dated Jul. 10, 2019.

* cited by examiner

SUCTION PUMP WITH OPTICAL STATUS INDICATOR

CROSS-REFERENCE TO RELATED APPLICATIONS

This present application is the US national phase of International Patent Application No. PCT/EP2020/050090, filed Jan. 3, 2020, which claims priority to European Application No. 19151005.6, filed Jan. 9, 2019. The priority application, EP 19151005.6, is hereby incorporated by reference in its entirety.

TECHNICAL FIELD

The present invention relates to a suction pump, particularly a breast pump for pumping human breast milk or a drainage pump for sucking body fluids, for example for thoracic drainage or for wound drainage.

PRIOR ART

Suction pumps of the type mentioned above are used in various areas, in particular as medical suction pumps for the suction of body fluids. For example, they are used as breast pumps for pumping human breast milk, wound or thoracic drainage or for sucking body fluids.

Medical suction pumps usually have a vacuum pump, one or more fluid collecting containers and a hose connection between patient and fluid collecting container. The hose connection is usually connected to a fluid collecting device, such as a breastshield or vacuum bandage, which rests on the patient's body. The vacuum pump creates a vacuum within the fluid collecting device, thereby drawing fluid from the body through the hose connection into the fluid collecting container. An example of a medical suction pump is disclosed in WO 2017/157691 A1.

In order to ensure proper operation of the suction pump, the operating parameters, in particular the vacuum applied and the filling level of the fluid collecting container, must be continuously monitored. For example, WO 2015/197462 A1 describes a medical suction pump with a filling level sensor for monitoring the filling level in the fluid collecting container.

Usually, known suction pumps have a display from which the current operating state of the suction pump can be read. However, this display can usually only be read at close range and from a certain viewing angle. On the one hand, this increases the work involved in monitoring a large number of suction pumps and also has the disadvantage that nursing staff also in sensitive areas such as intensive care or isolation wards sometimes have to approach the patient closely.

DESCRIPTION OF THE INVENTION

It is an object of the invention to provide a suction pump whose operating state can be easily read from a distance and from several viewing angles.

The suction pump according to the invention is a pump for sucking body fluids, such as a breast pump for pumping human breast milk or a drainage pump for wound or thoracic drainage. For example, a generic suction pump is disclosed in WO 2015/197462 A1 and WO 2017/157691 A1. A particularly preferred embodiment is a drainage pump for wound or thoracic drainage.

The suction pump according to the invention comprises an optical status indicator for displaying a light signal as a function of the operating state of the suction pump. According to the invention, the suction pump thus comprises at least one light source for generating the light signal. The optical status indicator can be itself in the form of a light source or it can be connected in a light conducting manner to a light source positioned at a different location of the suction pump.

According to a first variant of the invention, this status indicator is characterized in that it is arranged on at least two points of the outer surface of the suction pump, the surface normals of which are at an angle of at least 5° to one another. A surface normal is defined as a vector which is perpendicular to the respective point of the outer surface and which, viewed from the suction pump, is directed outwards.

To illustrate the arrangement of the status indicator according to the invention, reference is made to FIGS. 10A and 10B.

FIG. 10A schematically shows a suction pump 1 with an octagonal base area and eight, respectively flat side surfaces, each at an angle of 45° to the other. A status indicator 5 is arranged in the form of a continuous light band on all side surfaces. This status indicator is thus arranged, among other things, on four exemplarily selected points of the outer surface of the suction pump, whose surface normals 6a-d are plotted. The surface normals 6a and 6b are at an angle of 45° to each other, the surface normals 6a and 6c at an angle of 90° and the surface normals 6a and 6d at an angle of 180°. The angle enclosed between the outwardly pointing vectors is decisive in each case.

FIG. 10B schematically shows a suction pump 1 with a circular base area and a cylindrical basic shape. A status indicator 5 is arranged in the form of a continuous light band along the entire outer circumference of the suction pump. This status indicator is thus arranged, among other things, on three exemplarily selected points of the outer surface of the suction pump, the surface normals 6a-c of which are plotted. The surface normals 6a and 6b are at an angle of 90° to each other and the surface normals 6a and 6c at an angle of 180°.

In contrast to the suction pump according to the invention, conventional suction pumps have displays or illuminated switches to indicate the operating state, which are arranged only on a single flat surface of the pump housing and thus only on points of the outer surface, whose surface normals are parallel to each other and thus at an angle of less than 5° to each other.

By arranging the status indicator on at least two points of the outer surface of the suction pump according to the invention, the light signal is emitted in a wide viewing angle range and can therefore be easily seen also from a greater distance. This makes it easy to check the operating state of the suction pump.

The status indicator is arranged according to the invention on at least two points of the outer surface of the suction pump, the surface normals of which are at an angle of at least 5°, preferably at least an integer multiple of 5°, to at most 180° to each other, taking into ac-count the respectively smaller angle enclosed between two surface normals. For example, the surface normals are at an angle of at least 10° to each other, further preferably at least 15°, at least 20°, at least 25°, at least 30°, at least 35°, at least 40°, at least 45°, at least 50°, at least 60°, at least 70°, at least 80°, at least 90°, at least 110°, at least 130°, at least 150° or at least 170°. A particularly advantageous viewing angle is achieved by the status indicator being arranged on at least two points of the outer surface of the suction pump, the surface normals of which are at an angle of at least 45°, preferably at least 90°, particularly preferably at an angle of 180° to one another. Furthermore, it is particularly preferred if the status indicator is arranged on at least three points of the outer surface of the suction pump, the surface normals of which are in each case at an angle of at least 45°, preferably at least 90°, to one another.

Preferably, the points on which the status indicator is arranged are part of the suction pump housing. The status indicator can be arranged on the front side, i.e. the surface of the housing facing the user, on the rear side, on the top side, on the underside or on the side surfaces of the housing. The housing forms the outer enclosure of the suction pump. Within the scope of the present invention, the status indicator itself is not considered to be part of the outer surface of the suction pump and thus not part of the pump housing on which at least one of the two points is arranged. The status indicator does not necessarily have to be flush with the surface, but can also protrude spatially from the surface, for example in the form of an illuminated switch or a protruding lighting element.

For example, in a pump housing with an octagonal base area, the status indicator may be arranged on two neighboring side surfaces. The surface normals of the neighboring side surfaces are each at an angle of 45° to each other. In the case of a pump housing with a square base area and with the surface normals of neighboring side surfaces being each at an angle of 90° to each other, the status indicator can, for example, be arranged on two different, neighboring or opposite side surfaces. The status indicator does not necessarily have to be placed on a side surface, but can also be arranged for example on the top side of the pump housing.

According to a second variant of the invention, the suction pump according to the invention has one or more stands for support on a support surface. By these stands a defined distance is produced between the underside of the suction pump and the support surface. In this variant, the suction pump is characterized in that the status indicator is arranged on the underside of the suction pump so that the light signal is emitted in the direction of the support surface. In this case, the light signal is reflected from the support surface and guided through the gap between the underside of the suction pump and the support surface into the environment of the suction pump. In this way, the light signal is emitted over a wide range of viewing angles and can therefore also be clearly seen from a greater distance. This makes it easy to check the operating state of the suction pump. In a preferred embodiment, the status indicator is arranged on the underside of the suction pump in such a way that the light reflected from the support surface is emitted in a viewing angle range of at least 45°, preferably at least 90°, particularly preferably 180°, most preferred 360° in a horizontal plane around the suction pump.

According to a further alternative design of the present invention, the status indicator occupies at least 5%, preferably at least 10%, further preferably at least 20%, especially preferably at least 30% or more up to 100% of the surface of the suction pump. The surface is understood to be the total surface of the suction pump, i.e. also those parts of the surface that are not visible during normal operation since they form the underside on which the suction pump stands, or protrude from the stands, so that the undersurface of the support surface is opposite. The alternative accordingly specifies a status indicator that is provided over a relatively large surface on the outside of the suction pump, which increases the visibility of the status signal(s) emitted by the status indicator. The status indicator can only be provided on a side surface of the pump that is visible from the outside, e.g. only one of the side surfaces or the surface in the case of a cuboid or box-shaped design of the housing.

In a preferred embodiment, the suction pump has a pump housing that comprises a front surface, two adjacent side surfaces and a top surface. The side of the pump housing facing the user is designated as the front surface. The side surfaces laterally follow the front surface, the upper surface closes the pump housing upwards. Here the status indicator is arranged on at least two points of at least two of the said surfaces, whose surface normals are at an angle of at least 5° or at least an integer multiple of 5° but not more than 180° to each other. The surface normals are preferably positioned at an angle of at least 45°, particularly preferably at least 90° to each other.

A particularly good visibility of the status indicator is achieved by the fact that the status indicator is arranged on at least three of the named surfaces, for example the front surface and both side surfaces.

The said surfaces themselves are preferably flat, but can be at least partially rounded.

In one embodiment, the housing described is cuboid or box-shaped, so that the front surface, the adjoining side surfaces and the upper surface are at right angles to each other. In a variant of this embodiment, the upper surface may also be inclined and, for example, be at an angle of more or less than 90° to the front or one of the side surfaces.

The edges extending between the said surfaces need not necessarily be at right angles, but may also be beveled or rounded. The edges may be totally or partially beveled so that between two or more of the said surfaces there are additional inclined surfaces which, like the edges, may be provided with a status indicator or part thereof.

The pump housing can also have an outer surface that is at least partly round. For example, the pump housing could be cylindrical, cone-shaped, sphere-shaped or hemisphere-shaped. Also in this case the status indicator is mounted on at least two points of the outer surface, whose surface normals are at an angle of at least 5°, preferably at least an integer multiple of 5°, particularly preferably at least 45°, further preferably at least 90°, most preferred at an angle of 180° to each other.

The pump housing, for example, is made of plastic or aluminum. In particular, the pump housing is designed so that the exposed surfaces of the housing form an all-round sealing closure for the components arranged inside the pump housing. Usually only hoses and switches protrude from the pump housing if they are part of the pump. Optionally, only hose connectors for connecting corresponding hoses may protrude from the housing. Otherwise, the housing is usually flat so that it is easy to clean and disinfect. The housing either contains an autonomous power supply and/or is equipped with a connection cable for the electrical connection of the pump to the mains.

A particularly good visibility of the light signal is achieved by the fact that the status indicator on the said surfaces is formed in the form of light bands, which preferably extend between two edges of the surfaces. The light bands extend here at least in sections on said surfaces and/or the edges. Preferably, the light bands preferably extend continuously between two edges of said surfaces. Particularly preferably, the light bands extend continuously over at least two of the said surfaces. The light bands can, for example, run horizontally, vertically or obliquely in a straight line. Alternatively, the light bands can follow a curved contour, such as a wavy line. Preferably, the status indicator has the shape of a single light band that extends continuously over the front surface and the two side surfaces. This light band can, for example, run horizontally in a straight line or along a wavy line. Preferably, the light band forms a self-contained curve.

In an alternative embodiment, the status indicator on the said surfaces is in the form of one or more discrete lighting elements. Preferably, these are flat, non-point-shaped lighting elements. The lighting elements preferably comprise a diffuser element through which the light signal passes, so that the light intensity is homogeneously distributed over the entire illuminated surface of the lighting elements. The discrete lighting elements can for example be circular, ellipsoidal or rectangular in shape. The discrete lighting elements can also be in the form of self-contained light bands, i.e. e.g. ring-shaped. Preferably, there are at least two discrete lighting elements on each of the two side surfaces of the pump housing.

The status indicator is preferably designed to cover a large area and preferably occupies at least 5%, preferably at least 10%, particularly preferably at least 20%, most preferably at least 30% of the outer surface of the suction pump. Although it is conceivable that the entire outer surface of the suction pump is covered by the status indicator, the status indicator practically does not occupy more than 90%, preferably not more than 70%, particularly preferably not more than 50% of the outer surface.

In the case of a round housing, for example, the status indicator may be distributed in the form of several discrete lighting elements over the outer circumference of the round outer surface. Preferably, however, the status indicator is designed as a continuous light band which runs along at least part of the outer circumference of the housing over an angular range of 5° or more, preferably 45° or more. Preferably the light band runs over the whole circumference.

The pump housing itself can be a single piece or can consist of several interconnected housing parts. In a preferred design, the pump housing comprises two components, each with a front surface and two adjacent side surfaces, joined together along a horizontally extending seam. Here, the seam itself can be made of a translucent material which is illuminated from the inside and thus forms the optical status indicator.

In a further embodiment, the suction pump comprises a container for receiving a liquid. In particular, this is a fluid collecting container for the collection of the body fluid to be pumped off. This container is preferably detachably connected to the suction pump. In particular, the container is preferably a consumable and is replaced with a new container after use. Preferably, in the mounted state the outer wall of the container forms part of the outer surface of the suction pump. For example, the container may form a rear surface and two adjacent side surfaces which together form part of the outer surface of the suction pump.

In a preferred embodiment, the status indicator is arranged on the outer surface of the container. As described above, the status indicator can, for example, be in the form of one or more light bands or discrete lighting elements.

However, it is particularly preferred if the outer wall of the container or part of it is made of a translucent material which is illuminated from the inside. The container is illuminated according to the invention in such a way that the light signal exits outwards on at least two points of the outer surface of the container, whose surface normals are at the above-mentioned angle to one another. The outer wall of the container or parts thereof may, for example, be made of a light guide into which a light signal generated by a light source arranged inside the suction pump is fed and diverted to the outside via light deflecting structures in the light guide. The container may also be made of a transparent plastic material which is illuminated from the inside and/or outside, the light source usually being accommodated in or on the housing of the pump. This is particularly advantageous for disposable plastic containers which are disposed of after use.

In a further embodiment, the suction pump comprises a flow line to connect the suction pump to a fluid collecting device. Via the flow line, liquid can be drained from the patient via the fluid collecting device and collected, for example, in the container described above. The fluid collecting device is, for example, a breastshield or a vacuum bandage mentioned at the beginning. The flow line preferably comprises a coupling to connect it to a fluid collecting device or to a further piece of hose. The coupling is designed as a Luer or Luer-Lock connection, for example. The flow line can, for example, have a circular or rectangular cross-section, with a circular cross-section being preferred.

In a preferred configuration, the status indicator is mounted on the outer surface of the flow line so that it is arranged on at least two points of that outer surface whose surface normals are at an angle of at least 5°, preferably at least an integer multiple of 5°, particularly preferably at least 45°, most preferably at least 90° to each other. The status indicator may, for example, be in the form of one or more light bands or discrete lighting elements as described above. The light band can, for example, be wound around the flow line. It is particularly preferred if the status indicator is designed as a light band which completely encloses the outer circumference of the flow line. It is also particularly preferred if the outer wall of the flow line or part of it is made of a translucent material which is illuminated from the inside. The outer wall of the flow line or parts thereof can, for example, be made of a light guide into which a light signal generated by a light source arranged inside the suction pump is fed and diverted to the outside via light deflecting structures in the light guide. For example, the flow line can consist of a transparent plastic that serves as a light guide and is illuminated from inside and/or outside. Here, too, the light source is usually accommodated in or on the pump housing.

The light signal is generated by one or more light sources. For example, the suction pump can have a single light source whose light is transmitted via one or more light guides to the relevant points on the outer surface of the suction pump, where it passes through a translucent element to the outside. In this case, the status indicator is formed by the translucent elements arranged on the surface of the suction pump. In this case, an LED is a particularly suitable light source.

In one embodiment, a part of the outer surface of the suction pump consists of a translucent material into which the light signal generated by a light source arranged inside the suction pump is coupled. The light signal is then directed outwards via suitable light deflection structures within the translucent material.

The suction pump can also comprise several light sources arranged side by side on the relevant points of the outer surface and together forming the status indicator. For example, point-shaped LEDs can be used. These can, for example, be arranged in a row or in a grid.

Another suitable light source is OLEDs, which have the particular advantage of being applied in a flat form to the relevant points of the outer surface using thin-film technology.

In a preferred embodiment, the status indicator comprises one or more OLEDs arranged on the outer surface of the suction pump.

Suitable light-conducting elements or light sources for producing the status indicator according to the invention are known from the prior art and described, for example, in EP 3228931 A1, EP 3326863 A1, WO 2014/033686 A2, WO 2015/116743 A1, DE 10 2009 051 234 A1 and U.S. Pat. No. 6,728,464 A1.

Preferably, the light signal is guided through a diffuser element so that the light intensity is homogeneously distributed over the entire surface of the status indicator. This produces a uniform brightness of the light signal, which facilitates perception of the light signal from different viewing angles. In an alternative embodiment, the light intensity is distributed inhomogeneously over the surface of the status indicator. In this case, for example, the light signal can form a stripe pattern.

In one embodiment, the suction pump comprises a device for measuring the ambient brightness and adjusting the intensity of the light signal to the ambient brightness. The device preferably comprises a brightness sensor whose sensor signal is processed by a control unit of the suction pump to control the intensity of the light signal as a function of the determined ambient brightness. In this way, the brightness of the status indicator can be reduced at night in order to save energy and not disturb the patient's sleep. At the same time, the daytime brightness can be automatically increased to ensure good visibility of the status indicator.

The light signal indicated by the status indicator is generated or adjusted depending on the operating state of the suction pump. The operating state is preferably determined on the basis of one or more operating parameters. For example, these parameters include the filling level of the above-described container for receiving the body fluid, the vacuum present in the flow line described above or a hose connection or fluid collecting device connected to it, the flow rate measured in the flow line or a hose connection connected to it, or the battery charge level of a battery-powered suction pump. By comparing the measured operating parameter with a given reference value, it can be determined whether there is a malfunction of the suction pump and/or a deviation from the given process sequence.

An operational fault occurs, for example, if the filling level of the container exceeds a predetermined maximum, if the pump unit does not operate with the predetermined pump capacity or if the charge level of any battery present falls below a predetermined minimum. A deviation from the predetermined process sequence exists, for example, if a leak in the flow line or a hose connection connected to it or a leak in a vacuum bandage results in a changed flow rate.

The light signal is preferably triggered or adjusted automatically by a control unit arranged in the suction pump. Preferably, the light signal is triggered or adjusted in the event of an operational fault and/or a deviation from the predetermined process sequence, for example if the maximum filling level of the container is exceeded, the flow rate in the flow line or a hose connection connected thereto, or the vacuum present in the flow line deviates from a predetermined reference value or exceeds or falls below predetermined limit values.

The intensity of the light signal can be constant over time or vary periodically (flashing). Preferably, the control device can switch between these two alternatives depending on the severity of the malfunction. For example, a constant light signal can be generated when the filling level of the container approaches its maximum, and a flashing light signal when the filling level exceeds the maximum. The flashing frequency can also be increased to indicate a particularly severe malfunction.

In one embodiment, the light signal is generated in different colors depending on the operating state. For example, a light signal in one color (e.g. green) is generated during fault-free operation and a light signal in another color (e.g. red) is generated if there is a malfunction and/or a deviation from the predetermined process sequence. In this way, the operating personnel can easily check the operating state of the suction pump.

The status indicator can display a uniform light signal over its entire surface, the light signal conveying a single piece of status information. In this case, for example, the status indicator indicates whether there is a fault in the operating status or not. Alternatively, the status indicator can also be divided into different sections, each of which displays different light signals. In this way, different status information can be conveyed. For example, this can be used to differentiate between different types of malfunction.

The suction pump can be supplied with power via a mains connection or an internal battery. In the case of a battery, the suction pump can be configured to be portable and does not necessarily have to be operated in a stationary way. In the case of a battery, the suction pump preferably has a power connection which can be used to charge the battery.

Other preferred features of the invention result from the embodiments described below.

DESCRIPTION OF THE DRAWINGS

In the following, preferred embodiments of the invention are described on the basis of drawings, which only serve to explain the invention and are not to be interpreted restrictively. In the drawings.

DESCRIPTION OF PREFERRED EMBODIMENTS

Figures 1, 2:
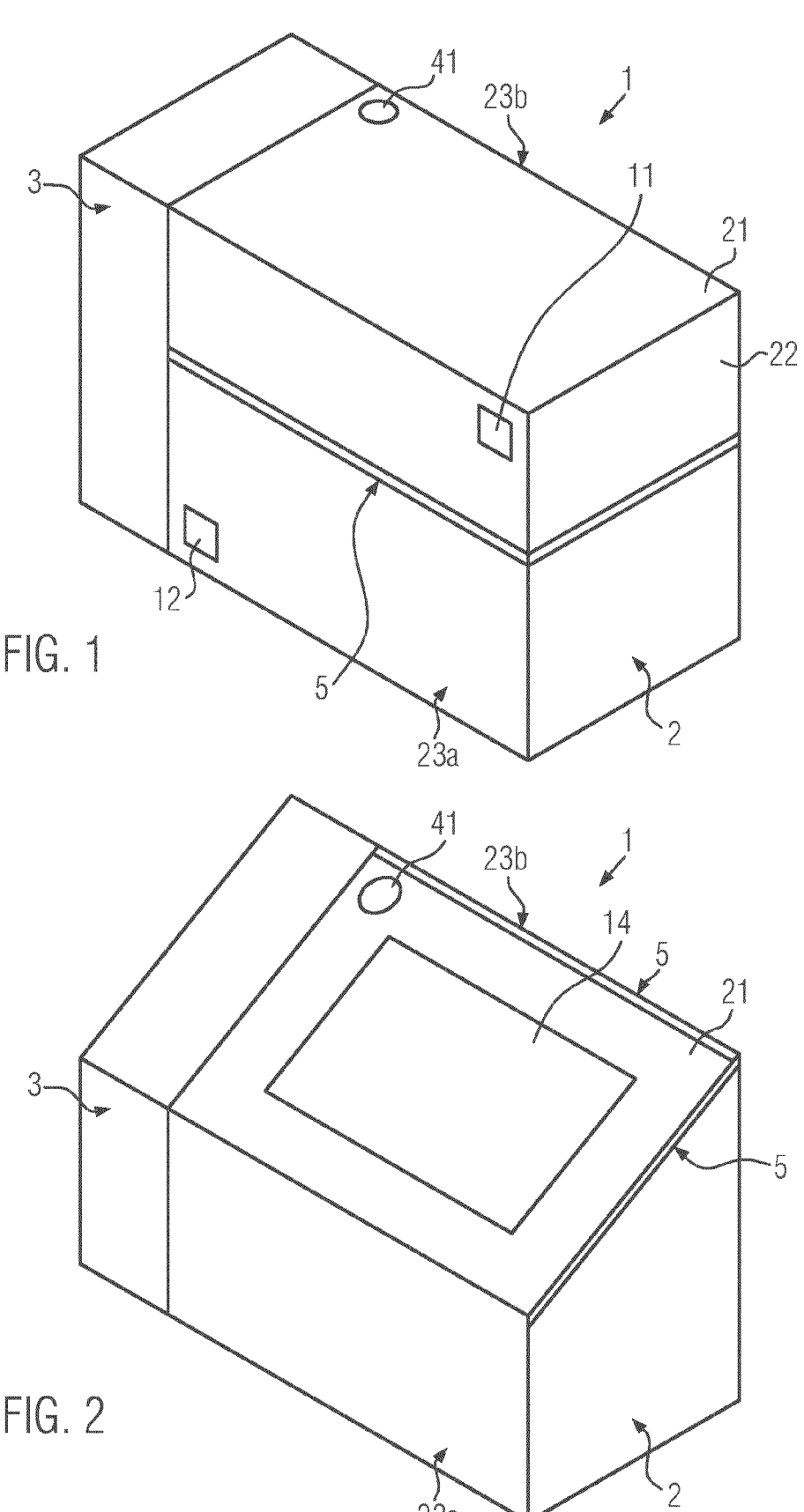
FIG. 1 is a schematic representation of a suction pump according to a first embodiment.
FIG. 2 is a schematic representation of a suction pump with inclined upper surface.

FIG. 1 shows a suction pump 1 for wound drainage according to the first variant of the invention. The pump has an on/off switch 11 and a power connection 12. One or more stands 13 not shown here may be provided on the underside of the suction pump 1 to place the suction pump 1 on a support surface.

In the suction pump 1 shown, the power supply is preferably provided via the power connection 12, which can be connected to the mains via a mains cable. Alternatively or in addition, the suction pump 1 can also have a battery for the power supply. In this case, the suction pump 1 can be configured to be portable and does not necessarily have to be operated in a stationary way. In this case, the battery can preferably be charged via the power connection 12.

The suction pump 1 has a box-shaped pump housing 2, which has an upper surface 21, a front surface 22 and two side surfaces 23a, 23b adjoining the front surface 22. The surface normals (not plotted) of the front surface 22, the upper surface 21 and the side surfaces 23a, 23b are each at an angle of 90° or 180° to one another. The pump housing 2, for example, can be made of plastic or aluminum. The pump housing is preferably made of plastic. The upper surface 21 can also have a display for displaying different operating parameters and/or a control panel for setting operating parameters.

A container 3 is mounted on the back of the suction pump 1. It is used to receive the pumped body fluid. The container with its outer walls forms part of the outer surface of the suction pump 1 and is flush with the upper surface 21 and the two side surfaces 23a, 23b of the pump housing 5. The container 3 is advantageously detachably connected to the suction pump 1 for replacement or emptying. For this purpose, the suction pump 1 has an unlocking mechanism. Advantageously, the suction pump 1 comprises a filling level sensor with which the quantity of liquid collected in the container 3 can be continuously measured and the measurement result can be transmitted to a control unit.

A flow line 4, not shown in FIG. 1, is provided on the upper side of the suction pump 1. It advantageously has a circular cross-section. The flow line 4 serves to connect the suction pump 1 to a liquid collecting device not shown here, such as a vacuum bandage. The flow line 4 is connected inside the pump housing 2 to a pump unit not shown here for generating a vacuum and to the container 3. The flow line 4 is led out of the housing via a hose receiving opening 41 on the upper side of the suction pump 1. At its distal end, the flow line 4 can have a coupling which serves the connection to the liquid collecting device, preferably via a further hose line.

An optical status indicator 5 is arranged in the form of a continuous light band on the front surface 22 and the two side surfaces 23a, 23b. This light band extends from the rear edge of the one side surface 23a to the rear edge of the opposite side surface 23b.

The status indicator 5, for example, lights up when there is a fault in the suction pump 1. This is the case, for example, if a suitable filling level sensor detects that the maximum filling level of the container 3 has been exceeded, or if a suitable pressure sensor detects a deviation of the negative pressure within the flow line 4 from previously defined limit values.

In an advantageous design of the status indicator 5, said indicator shines in different colors depending on the operating state. For example, the status indicator 5 shines in a certain color if there is no fault, and in a different color if a fault has been detected.

The status indicator 5 is advantageously integrated into the material of the pump housing 5, e.g. a part of the pump housing is made of translucent material into which the light signal generated by an internal light source, e.g. an LED, is coupled via a light guide. The light signal is advantageously coupled in such a way that the light intensity is homogeneously distributed over the entire length of the status indicator 5. Alternatively, the light intensity can also be distributed unevenly over the length of the status indicator 5. For example, the light may have a band pattern.

The suction pump 1 advantageously comprises a brightness sensor (not shown) for measuring the ambient brightness and a control unit connected to it which adjusts the brightness of the status indicator 5 to the respective ambient brightness.

FIGS. 2 to 7 show variants of the suction pump 1 shown in FIG. 1.

According to FIG. 2, the suction pump 1 has a pump housing 2 with an obliquely extending upper surface 21. A status indicator 5 is arranged in the form of light bands both on the upper surface 21 and on a side surface 23a of the housing. In addition, a display 14 can be arranged on the upper surface 21. The display 14 can be used to display further information on the operating state of the suction pump 1. The display can also be designed as a touch-sensitive screen which allows the user to control the function of the suction pump 1. As a modification of the suction pump 1 shown in FIG. 1, the container 3 is not arranged on the back of the suction pump 1, but on the side.

Figures 3, 4:
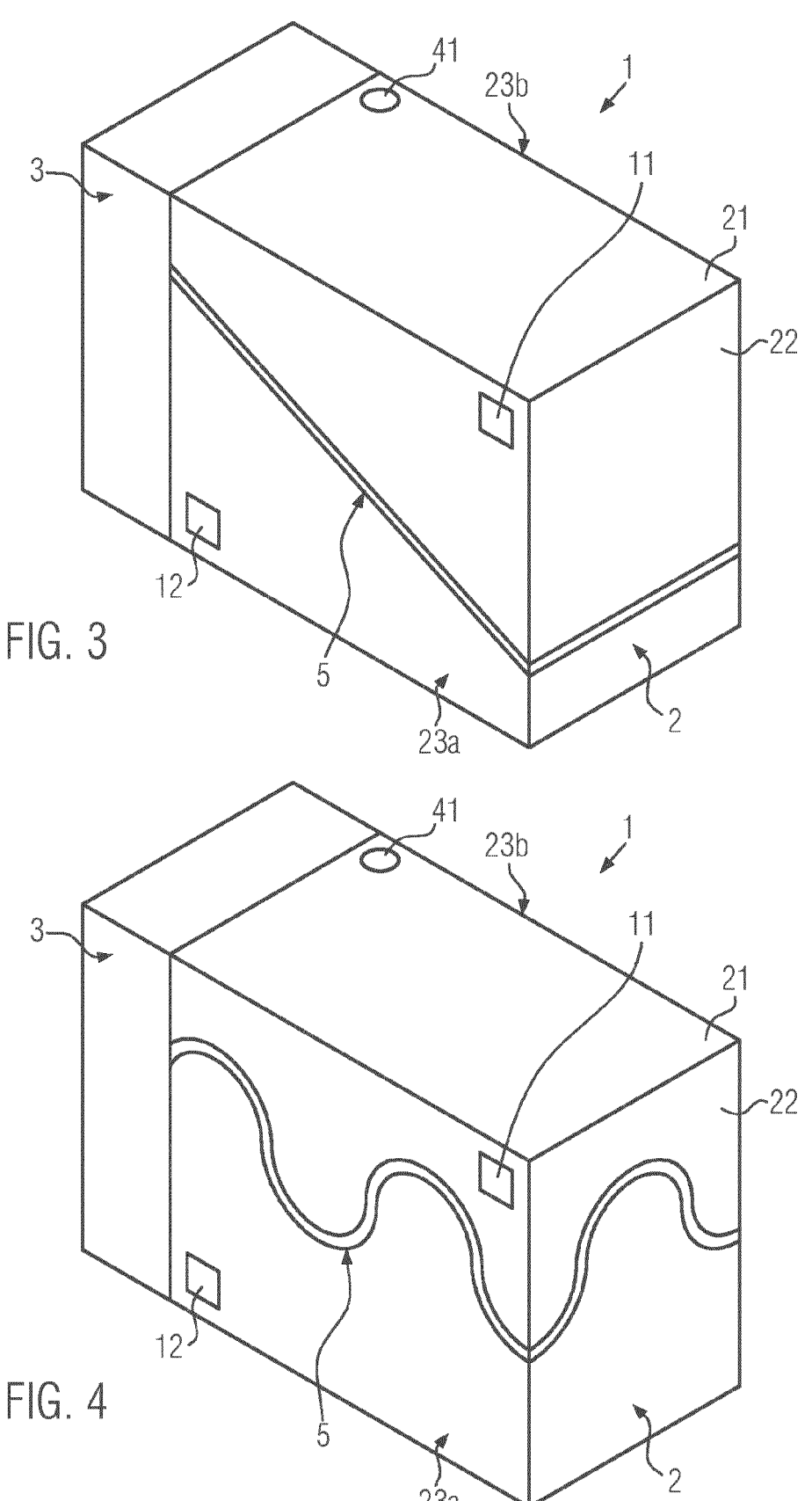
FIG. 3 is a schematic representation of a suction pump with a status indicator in the form of a continuous light band on the front surface and on the two side surfaces of the pump housing.
FIG. 4 is a schematic representation of a suction pump with a status indicator in the form of a continuous light band on the front surface and on the two side surfaces of the pump housing.

FIGS. 3 and 4 show a status indicator 5 which extends in the form of a light band over the front surface 22 and the two side surfaces 23a, 23b of the pump casing 2. In FIG. 3 the status indicator 5 runs in an oblique line over the two side surfaces 23a, 23b and in a horizontal line over the front surface 22. In FIG. 4 the status indicator 5 runs along a wavy line.

Figures 5, 6:
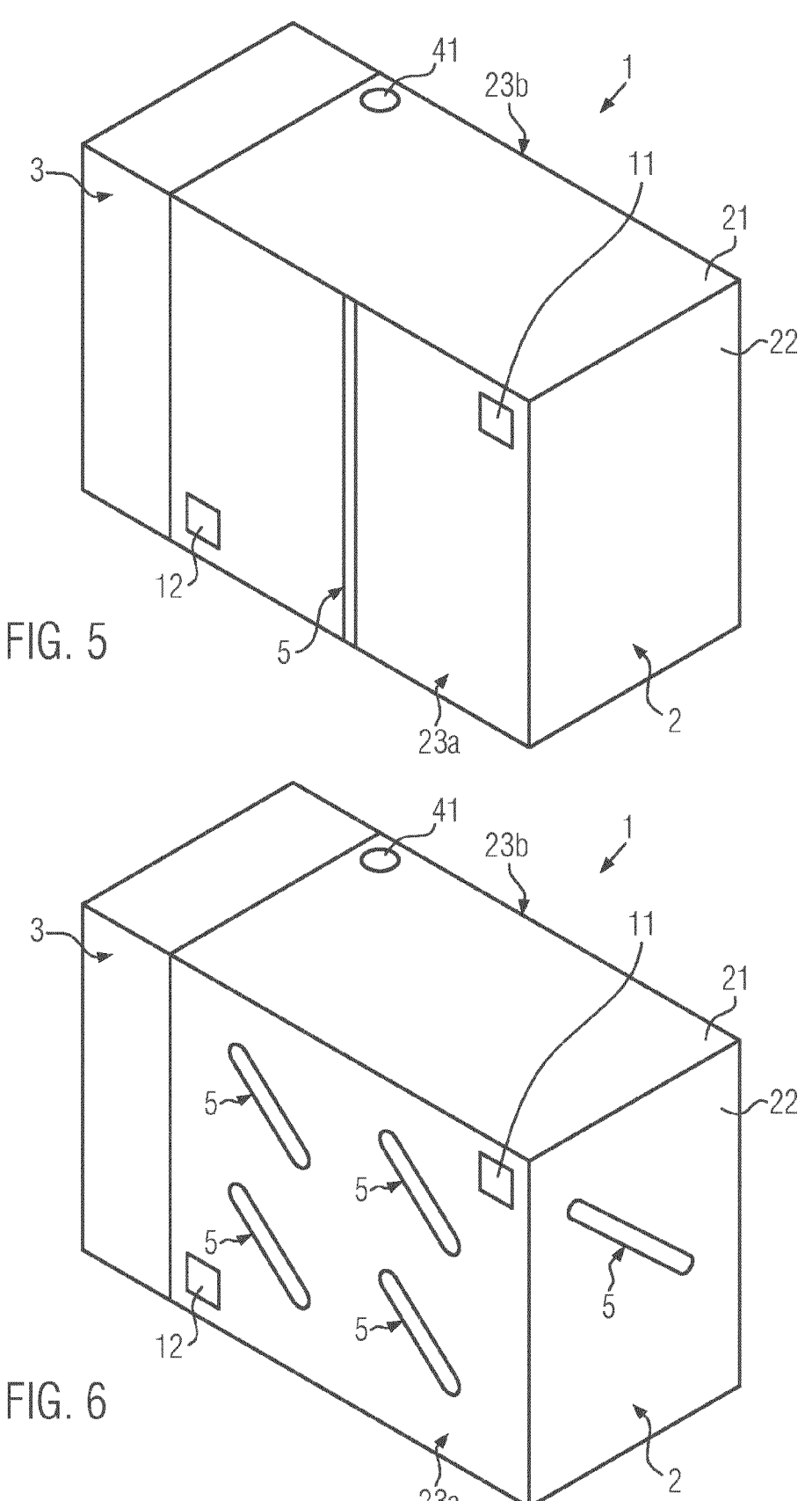
FIG. 5 is a schematic representation of a suction pump with a status indicator in the form of a light band on the two side surfaces of the pump housing.
FIG. 6 is a schematic representation of a suction pump with a status indicator in the form of discrete lighting elements.

FIG. 5 shows a status indicator that is respectively provided in the form of two continuous vertical light bands on the two side surfaces 23a and 23b. There is no status indicator on the front side 22.

Figures 7, 8:
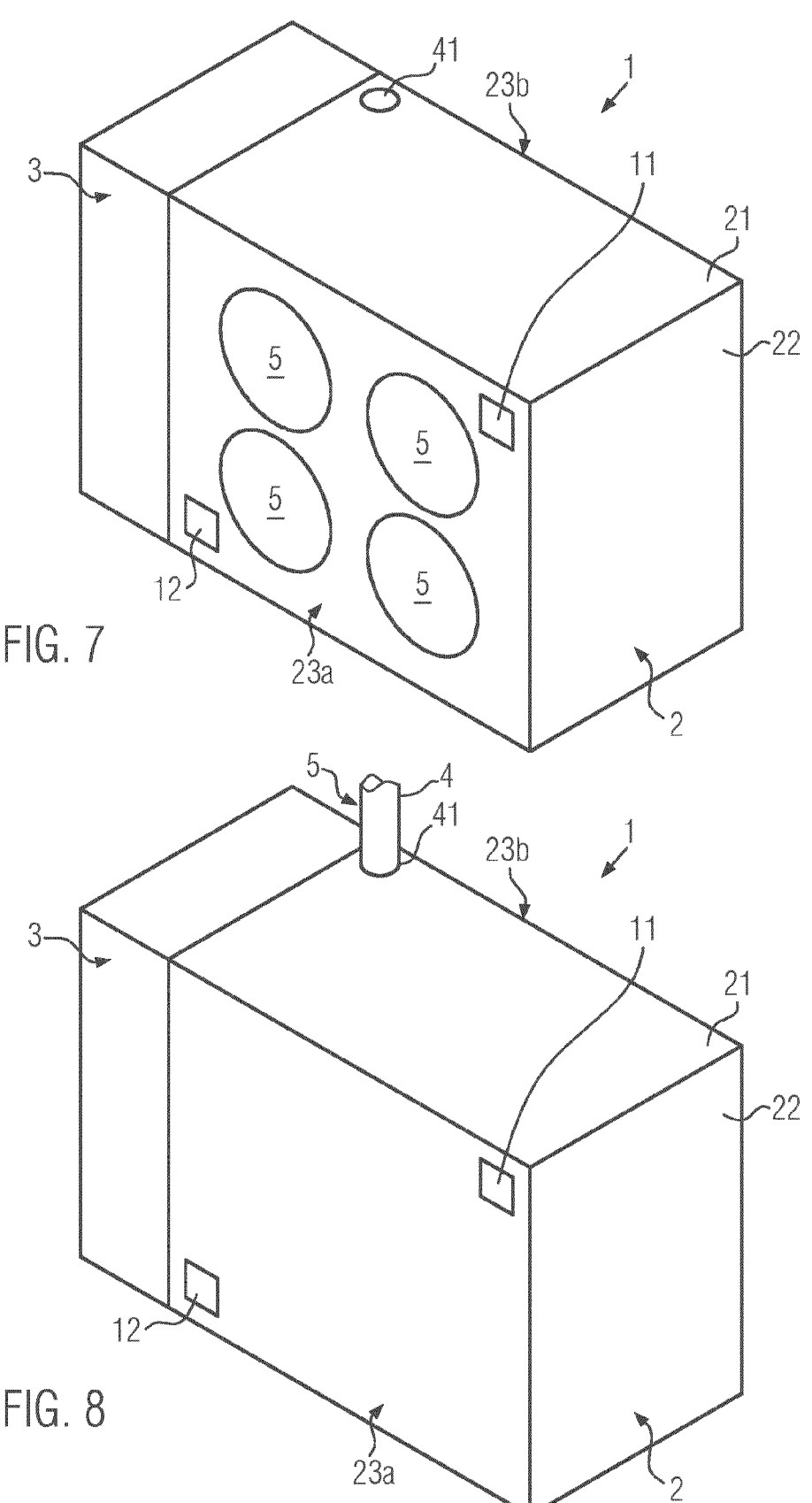
FIG. 7 is a schematic representation of a suction pump with a status indicator in the form of discrete lighting elements.
FIG. 8 is a schematic representation of a suction pump with a status indicator mounted on the outer surface of the flow line.

FIGS. 6 and 7 show a status indicator 5 in the form of a large number of discrete lighting elements. In FIG. 6, these lighting elements have the shape of elongated rectangles with rounded edges and are attached to the two side surfaces 23a, 23b and also to the front surface 22. In FIG. 7, the lighting elements are circular and only mounted on the two side surfaces 23a, 23b.

FIG. 8 shows another embodiment of the invention in which the flow line 4 is made of a translucent material which is illuminated from the inside. The flow line 4 has a circular cross-section. The light signal generated by a light source (not shown here) which is arranged inside the suction pump 1 is fed into the translucent material via light guides. The translucent material can extend over the entire length of the flow line 4, or only part of the flow line 4, for example the section between the hose receiving opening 41 and the coupling 42, can be made of the translucent material. In this way, at least part of the outer surface of the flow line 4 serves as an optical status indicator 5 over the entire outer circumference.

Figures 9, 10A, 10B:
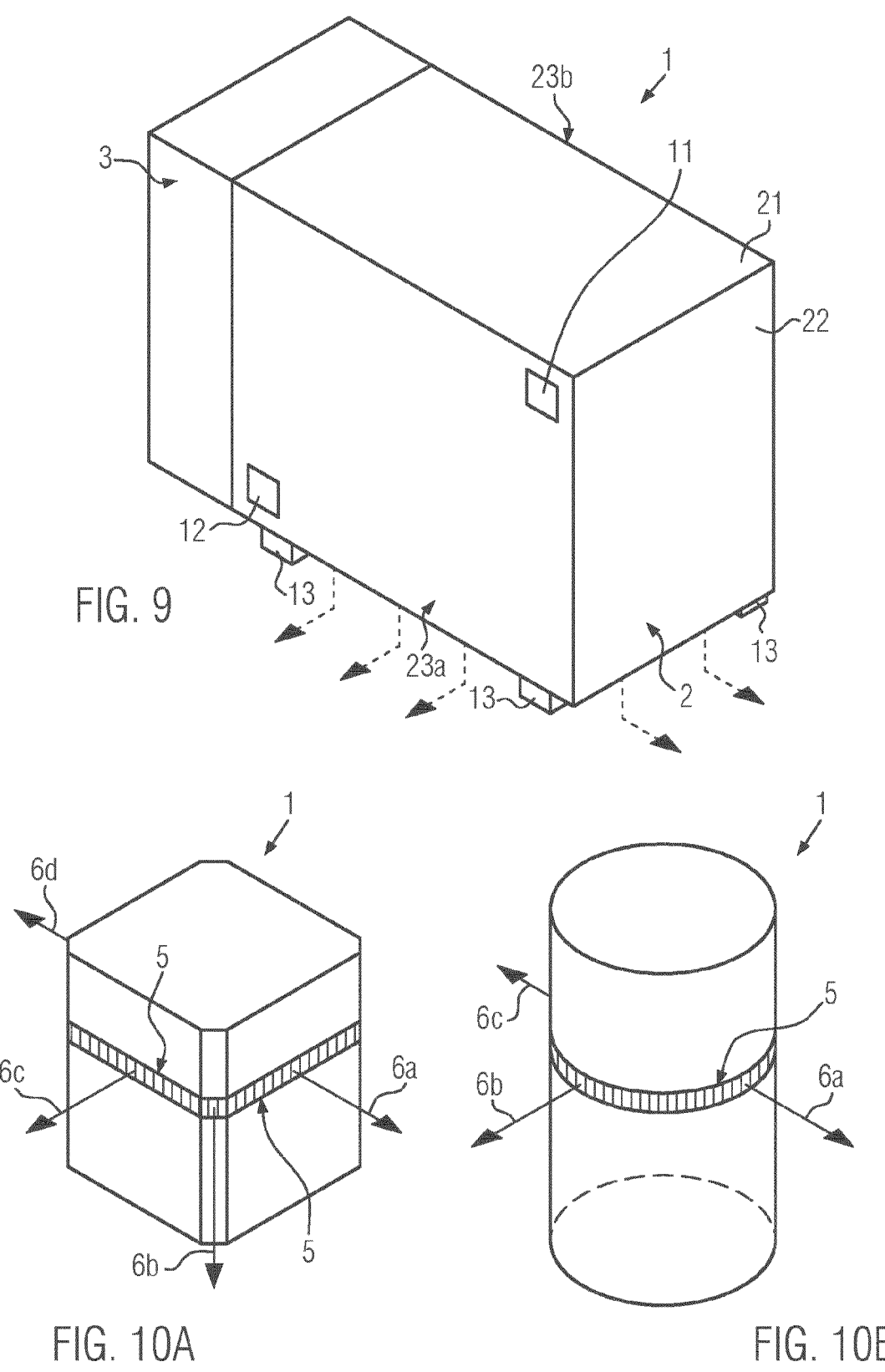
FIG. 9 is a schematic representation of a suction pump according to the second variant of the invention with a status indicator mounted on the underside of the suction pump.
FIG. 10A is a schematic representation of a suction pump according to the first variant of the invention with an octagonal base area.
FIG. 10B is a schematic representation of a suction pump according to another variant of the invention with a round base area.

FIG. 9 shows a suction pump 1 according to the second variant of the invention. The suction pump comprises a housing 2, a container 3, a flow line 4, an on/off switch 11 and a power connection 12 as already described for the suction pump of FIG. 1. The suction pump 1 also has stands 13 on its underside, which can be used to place the suction pump 1 on a support surface. The stands 13 have the effect that a defined distance is created between the support surface and the underside of the suction pump 1. An optical status indicator 5 is mounted on the underside of the suction pump 1 so that the light signal indicated by the status indicator 5 is emitted in the direction of the support surface. The light signal shown in the drawing by the dotted arrows is reflected by the support surface and directed outwards through the gap between suction pump 1 and support surface.

LIST OF REFERENCE NUMERALS 1 suction pump
11 on/off switch
12 power connection
13 stand
14 display
2 pump housing
21 upper surface
22 front surface
23*a*, 23*b* side surfaces
3 container
4 flow line
41 hose receiving opening
5 status indicator
6*a-d* surface normals

The invention claimed is:

1. A suction pump for sucking body fluid, comprising an optical status indicator for displaying a light signal as a function of an operating state of the suction pump and a container for receiving a liquid, the light signal guided through a diffuser element homogeneously distributing light intensity over an entire surface of the optical status indicator, and the optical status indicator arranged on at least two points of an outer surface of the suction pump, the surface normals of which are at an angle of at least 45° to one another, wherein the operating state of the suction pump is determined on the basis of two or more operating parameters including a filling level of the container and a battery charge level of the suction pump, the suction pump being supplied with power via an internal battery.

2. The suction pump according to claim 1, the suction pump having on an underside of the suction pump at least one stand for support on a support surface, the status indicator arranged on the underside of the suction pump so that the light signal is emitted in the direction of the support surface.

3. The suction pump according to claim 1, the status indicator occupying at least 5% of the outer surface of the suction pump.

4. The suction pump according to claim 1, wherein the suction pump comprises a pump housing comprising an upper surface, a front surface, and two respectively adjoining side surfaces, wherein the upper surface, the front surface, and the two respectively adjoining side surfaces form part of the outer surface of the suction pump, and the status indicator is arranged on at least two points of at least two of said surfaces.

5. The suction pump according to claim 4, wherein the status indicator is arranged at least on the front surface and the two side surfaces of the pump housing.

6. The suction pump according to claim 4, wherein the status indicator on at least two of said surfaces is respectively designed as a continuous light band or a light band divided into sections.

7. The suction pump according to claim 4, wherein the status indicator is one of a continuous light band or a light band divided into sections, which extends at least on the front surface and the two side surfaces of the pump housing.

8. The suction pump according to claim 4, wherein the status indicator is designed on at least two of said surfaces in the form of one or more discrete lighting elements.

9. The suction pump according to claim 1, wherein the suction pump comprises at least one light source for generating the light signal, wherein the light signal is passed on to the status indicator by an outer wall of a flow line of the suction pump, which outer wall serves as a light guide.

10. The suction pump according to claim 1, wherein the status indicator comprises one or more OLEDs as a source of the light signal.

11. The suction pump according to claim 1, wherein the suction pump comprises a device for measuring ambient brightness and for adjusting an intensity of the light signal to the ambient brightness.

12. The suction pump according to claim 1, wherein the light signal is one of generated or adjusted in the presence of at least one of a malfunction of the suction pump and a deviation from a predetermined process sequence.

* * * * *